US012575996B2

(12) United States Patent
Temporelli

(10) Patent No.: US 12,575,996 B2
(45) Date of Patent: Mar. 17, 2026

(54) ORTHOPAEDIC DEVICE COMPRISING AT LEAST ONE ACTUATOR

(71) Applicant: Robin Temporelli, Labége (FR)

(72) Inventor: Robin Temporelli, Labége (FR)

( * ) Notice: Subject to any disclaimer, the term of this patent is extended or adjusted under 35 U.S.C. 154(b) by 946 days.

(21) Appl. No.: 17/826,157

(22) Filed: May 26, 2022

(65) Prior Publication Data

US 2022/0402117 A1    Dec. 22, 2022

(30) Foreign Application Priority Data

May 26, 2022    (FR) ..................................... 21 05545

(51) Int. Cl.
*B25J 9/00* (2006.01)
*A61H 3/00* (2006.01)
*A61F 5/01* (2006.01)

(52) U.S. Cl.
CPC .............. *A61H 3/00* (2013.01); *B25J 9/0006* (2013.01); *A61F 2005/0139* (2013.01); *A61H 2003/007* (2013.01); *A61H 2201/1246* (2013.01); *A61H 2201/149* (2013.01); *A61H 2201/165* (2013.01); *A61H 2201/5064* (2013.01); *A61H 2201/5071* (2013.01)

(58) Field of Classification Search
CPC ................ A61H 3/00; A61H 2003/001; A61H 2203/007; A61H 2201/12; A61H 2201/1007; A61H 2201/123; A61H 2201/1238; A61H 2201/1246; A61H 2201/149; A61H 2201/1463; A61H 2201/164; A61H 2201/1645; A61H 2201/165; A61H 2201/1652; A61H 2201/1671; A61H 2201/1676; A61H 2201/5007; A61H 2201/5051; A61H 5501/5056; A61H 2201/5058; A61H 2201/5084; B25J 9/0006; B25J 9/12; B25J 9/123; B25J 9/144; B25J 9/14
See application file for complete search history.

(56) References Cited

U.S. PATENT DOCUMENTS

| | | | |
|---|---|---|---|
| 593,871 A | 11/1897 | Alexander | |
| 10,517,788 B2 | 12/2019 | Lee et al. | |
| 2014/0358053 A1 | 12/2014 | Triolo et al. | |
| 2019/0070061 A1* | 3/2019 | Choi ......................... A61H 3/00 |
| 2020/0069441 A1* | 3/2020 | Larose ...................... A61F 2/70 |
| 2020/0206899 A1* | 7/2020 | Storz ....................... B25J 9/144 |
| 2022/0362898 A1* | 11/2022 | Staroveski ............. B23Q 15/18 |

* cited by examiner

*Primary Examiner* — Jerrah Edwards
*Assistant Examiner* — Teresa M Dudden
(74) *Attorney, Agent, or Firm* — NIXON & VANDERHYE

(57) ABSTRACT

An orthopaedic device includes an upper exoskeleton (2, 4) and a lower exoskeleton (6), and a receiving actuator having a pivot-connection member (10). The exoskeleton is hinged with respect to one another via the pivot-connection member. A receiving transmission device (30) is designed to be able to transmit a movement to the pivot-connection member. At least a first hydraulic cylinder (20) is coupled to the receiving transmission device so as to be able to rotate said pivot-connection member. An emitting actuator has at least a first hydraulic emitting cylinder (51, 55), an emitting transmission device (60), and a motor device (70) coupled to the emitting transmission device. At least one pressurized-fluid-guiding line (42, 45) is designed to allow a hydraulic transmission of movement from the first emitting cylinder to the receiving actuator.

13 Claims, 7 Drawing Sheets

Fig 4a
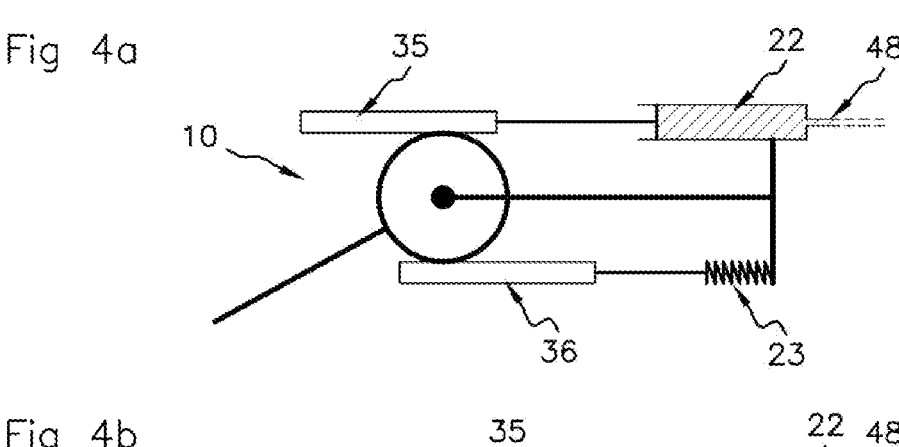
Fig 4b
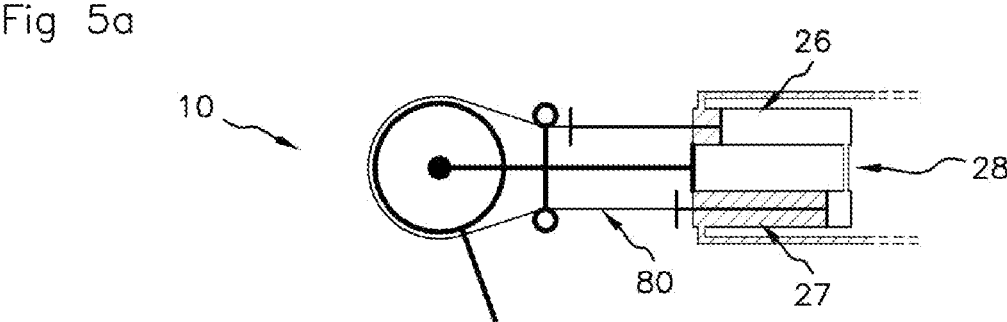
Fig 5a
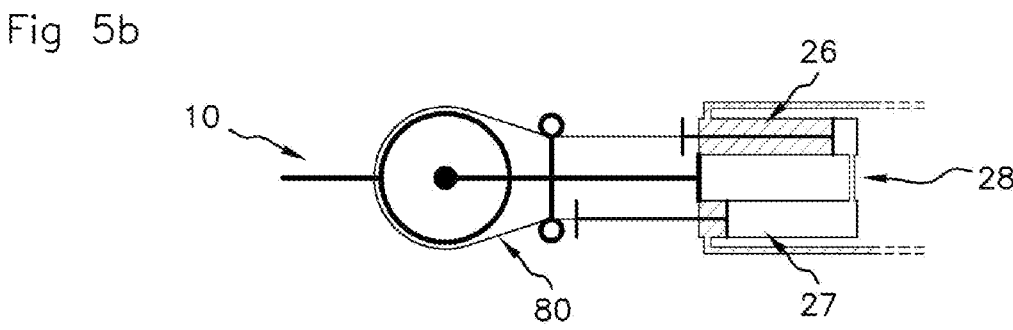
Fig 5b

Fig 6a
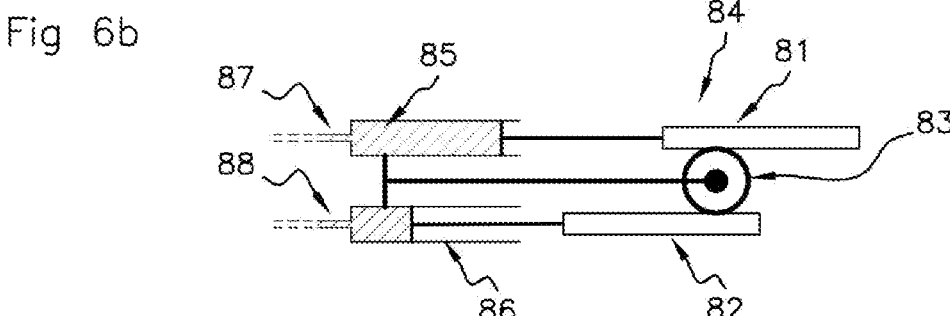
Fig 6b
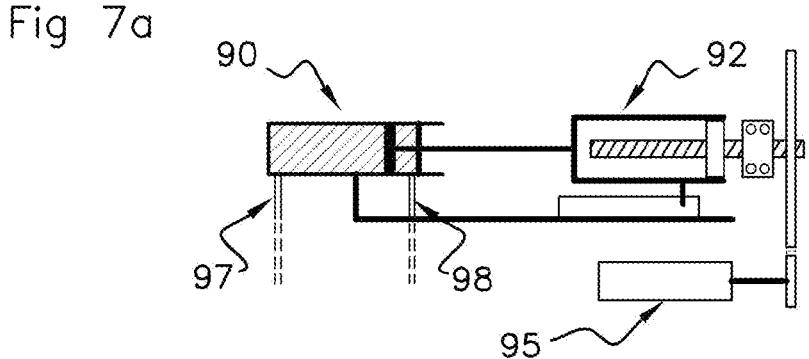
Fig 7a
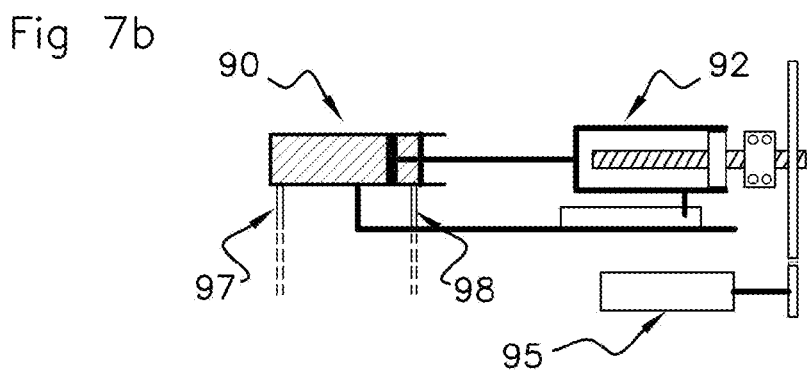
Fig 7b

ORTHOPAEDIC DEVICE COMPRISING AT LEAST ONE ACTUATOR

RELATED APPLICATION

This application relates to and claims the benefit of priority from French Patent Application No. 21 05545, filed on May 27, 2021, the entirety of which is incorporated by reference.

TECHNICAL FIELD

The invention relates to an orthopaedic device comprising at least one actuator. The invention relates in particular to such an orthopaedic device for a human lower limb.

An orthopaedic device according to the invention is useful for people with mild motor impairments (short-term or long-term), for example individuals with certain neurological pathologies, individuals with certain osteoarticular pathologies, or else individuals having short-term muscular atrophy. The invention may also be useful for individuals requiring muscular support to perform work, and in particular what is sometimes referred to as ground bracing.

Throughout the text, what is understood by "orthopaedic device" is any device intended to support a human limb, and/or to overcome functional deficiencies of a human limb, or, possibly, any device intended to at least partially replace a human limb.

PRIOR ART

So called active leg orthoses, for partly powering the bending and/or extension of a leg are known.

WO 2016/171548, for example, describes a prosthetic actuator comprising a hydraulic or pneumatic cylinder connected to an upper part and to a lower part of a leg, an automatic valve, an energy accumulator and a motion detecting sensor.

The known orthopaedic devices are generally heavy and bulky, the mass and the volume of such devices often being poorly distributed over the body of the user.

Such orthopaedic devices do not have bespoke orthoses and do not adapt to the disability and to the body shape of the user.

Such orthopaedic devices are also expensive and remain accessible only to an elite or to certain specialized rehabilitation centres. Thus, the bespoke and daily support and/or rehabilitation and/or assistance provided by an active orthopaedic device remains a little- and poorly addressed need for humans nowadays, whilst demand is increasing.

OBJECTS AND SUMMARY

The invention aims to overcome all of these drawbacks.

The invention aims to propose an orthopaedic device according to the invention which is minimally invasive and ergonomic (lightweight and compact) for a user.

The invention also aims to propose a certain balance in the distribution of the mass and the volume of the orthopaedic device over the body in order to make it comfortable for the user.

The invention also aims to propose such an orthopaedic device which is particularly discreet when it is worn by a user.

The invention also aims to propose such an orthopaedic device which is bespoke and therefore adapted to the disability and to the body shape of the user.

The invention also aims to propose such an orthopaedic device having a limited cost in order to make it accessible to the greatest number of people and for everyday use.

The invention also aims to propose such an orthopaedic device which is useful for users of various ages and having a wide variety of pathologies or in need of motor assistance and endurance.

The invention also aims to propose a method for implementing such an orthopaedic device.

The invention relates to an orthopaedic device, in particular for a human lower limb, characterized in that it comprises:

- at least one portion, referred to as upper exoskeleton, suitable for forming an abutment in contact with a first part of the human body,
- at least one portion, referred to as lower exoskeleton, suitable for forming an abutment in contact with a second part of the human body,
- an actuator, referred to as receiving actuator, comprising:
  - a pivot-connection member having at least one pivot axis, said upper exoskeleton and said lower exoskeleton being hinged with respect to one another via said pivot-connection member,
  - a receiving transmission device designed to be able to transmit a movement to said pivot-connection member,
  - at least a first hydraulic cylinder, referred to as first receiving cylinder, coupled to said receiving transmission device so as to be able to rotate said pivot-connection member,
- an actuator, referred to as emitting actuator, comprising:
  - at least a first hydraulic cylinder, referred to as first emitting cylinder,
  - an emitting transmission device designed to be able to transmit a movement to said first emitting cylinder,
  - a motor device coupled to said emitting transmission device so as to be able to drive said first emitting cylinder,
- at least one pressurized-fluid-guiding hydraulic line designed to allow a hydraulic transmission of movement from said emitting actuator to said receiving actuator.

An orthopaedic device according to the invention thus makes it possible, in particular by virtue of the use of such a pressurized-fluid-guiding hydraulic line, to be able to offset the emitting actuator with respect to the receiving actuator, that is to say the power unit of the orthopaedic device with respect to a human joint such as the knee, the elbow or else the hip. This makes it possible to reduce the mass of the orthopaedic device supported by the user's lower limb and also its bulk (volume). Specifically, it is thus possible to position the assembly formed by the emitting actuator, not on the lower limb but for example on the belt or else in a backpack carried by the user. The inventors have observed that this makes it possible to improve the user's feelings of stability and comfort such that their movements are made easier and are more natural.

The electrohydraulic mechanism comprising the assembly formed by said receiving actuator, said emitting actuator and said at least one pressurized-fluid-guiding line is designed to be able to be mechanically connected to different designs of said upper exoskeleton and lower exoskeleton.

In the case where the orthopaedic device is an orthosis for the knee, the upper exoskeleton may be arranged at least partly around the thigh of said limb and the lower exoskeleton may be arranged at least partly around the calf of said limb.

According to some embodiments, said orthopaedic device according to the invention is an orthosis, in particular an orthosis intended to be used for equipping the leg of a user so as to support the joint formed by the knee. The orthopaedic device according to the invention may thus support the bending and extension movements of a leg.

According to some embodiments, said lower exoskeleton also comprises a portion, referred to as plantar portion, designed to receive at least partly the sole of the foot. Thus, said lower exoskeleton may be designed so as to place said orthopaedic device fully or partially in connection with the ground, the mass of said orthopaedic device then being completely or partially self-supporting.

According to some embodiments, said orthopaedic device according to the invention may be designed to be able to equip an existing orthosis, the existing orthosis then forming said upper exoskeleton and/or said lower exoskeleton. The orthopaedic device according to the invention may thus be accommodated in such an orthosis, or else in a prosthesis.

According to some embodiments, said emitting actuator comprises a second hydraulic cylinder, referred to as second emitting cylinder.

According to some embodiments, said first emitting cylinder of said emitting actuator is a single-acting cylinder. According to some embodiments, said first emitting cylinder of said emitting actuator is a double-acting cylinder.

According to some embodiments, said second emitting cylinder of said emitting actuator is a single-acting cylinder. According to some embodiments, said second emitting cylinder of said emitting actuator is a double-acting cylinder.

According to some embodiments, said emitting transmission device is selected from the group formed by mechanical transmissions designed to be able to transform a rotational movement transmitted by said motor device into a translational movement of a piston of said first emitting cylinder.

According to some embodiments, said emitting transmission device is selected from the group formed by mechanical transmissions of the screw-nut type and mechanical transmissions of the pinion-rack type.

Each emitting actuator comprises at least one mechanical-energy-generating motor device, which may differ in nature: for example an electric motor and/or hydraulic motor and/or pneumatic motor, etc.

According to some embodiments, said motor device of said emitting actuator is an electric motor. It may be for example an electric motor powered by an electrical energy accumulator, such as an electric battery, in particular a rechargeable electric battery.

According to some embodiments, said receiving actuator comprises a second hydraulic cylinder, referred to as second receiving cylinder.

According to some embodiments, said first receiving cylinder of said receiving actuator is a single-acting cylinder. According to some embodiments, said first receiving cylinder of said receiving actuator is a double-acting cylinder.

According to some embodiments, said second receiving cylinder of said receiving actuator is a single-acting cylinder. According to some embodiments, said second receiving cylinder of said receiving actuator is a double-acting cylinder.

According to some embodiments, said receiving transmission device is selected from the group formed by mechanical transmissions designed to be able to transform a translational movement transmitted by said receiving actuator into a rotational movement of said pivot-connection member.

According to some embodiments, said receiving transmission device is selected from the group formed by mechanical cable and/or belt transmissions, transmissions of the rod-crank type, and mechanical transmissions of the pinion-rack type.

Said pivot-connection member has at least one axis of rotation, referred to as pivot axis. Said pivot-connection member may have one or more axes of rotation (monocentric or polycentric axes). According to some embodiments, said pivot-connection member is polycentric. Such a polycentric pivot-connection member makes it possible to better reproduce the kinematics of the knee, for example, and thus helps to improve the ergonomics of the orthopaedic device according to the invention.

According to some embodiments, said pivot-connection member comprises a bottom toothed wheel fixed to a lever connected to said lower exoskeleton. Said lever may be in the form of a bar having multiple curved and/or straight portions juxtaposed with one another.

According to some embodiments, the lever of said pivot-connection member is designed to permit at least two portions of said metal bar to rotate with respect to one another about an axis orthogonal to said pivot axis. Thus, said connection member may also exhibit one or more degrees of adjustment out of the plane, in order to be able to better adapt to the user's gait.

According to some embodiments, an orthopaedic device according to the invention comprises two pressurized-fluid-guiding hydraulic lines, in particular each line being connected to a cylinder of each actuator. Each pressurized-fluid-guiding hydraulic line makes it possible to transmit movement from an emitting cylinder to a receiving cylinder.

According to some embodiments, an orthopaedic device according to the invention comprises at least one sensor selected from the group formed by accelerometers, position sensors, pressure sensors, twisting-torque sensors, force sensors and deformation sensors.

According to some embodiments, an orthopaedic device according to the invention comprises an electronic unit and a man/machine interface. The man/machine interface may comprise any type of display screen. The man/machine interface allows a user to define the operating parameters of the orthopaedic device but also to display some biomarkers characteristic of the bio-kinematics of the human; for example for the lower limbs: type and number of cycles performed (walking, climbing staircases, sitting/standing up), mechanical power developed; for example for walking in particular: stride length, contact time, double-contact time, flight time, number of steps, distance travelled, speed, etc. The electronic unit comprises an electrical energy accumulator, such as an electric battery, which supplies it with power.

Each sensor is designed to transmit data representative of the operation of the orthopaedic device to said electronic unit. The operation of the orthopaedic device is controlled according to control loops taking into account these data and the parameters selected by the user via the man/machine interface.

The man/machine interface may likewise comprise a connection unit for connection to at least one link for communicating digital data with at least one remote server.

According to some embodiments, each exoskeleton of said orthopaedic device is formed of at least one material selected from the group formed by polymer materials, composite materials, and mixtures thereof.

According to some embodiments, each exoskeleton of said orthopaedic device is formed of at least one composite material comprising at least one reinforcement in the form of fibres and at least one polymer material within which the fibres extend.

The invention likewise relates to a method for implementing such an orthopaedic device. In particular, the invention relates to a method for implementing such an orthopaedic device in which:

said upper exoskeleton and said lower exoskeleton are joined to said receiving actuator, said upper exoskeleton and said lower exoskeleton are put in place on a human lower limb so as to equip a user with the receiving actuator of said orthopaedic device, said emitting actuator is installed on said user, said emitting actuator being connected to said receiving actuator, the electronic unit is started up and the man/machine interface is used to select the desired operating parameters.

The emitting actuator may be carried by the user of the orthopaedic device according to the invention in various ways allowing said emitting actuator to be offset from said receiving actuator and from the joint in question. According to some embodiments, the emitting actuator may be installed (including the electronic unit) in a bag that can be worn around the waist, close to the pelvis of the user of said orthopaedic device, or else in a backpack worn by the user of said orthopaedic device, or else fixed to the belt of the user of said orthopaedic device.

The invention likewise relates to a method for manufacturing such an orthopaedic device.

The invention likewise relates to an orthopaedic device and a method characterized, in combination or individually, by all or some of the features mentioned above or below. Irrespective of the formal presentation given, unless explicitly indicated otherwise, the various features mentioned above or below should not be considered to be intrinsically or inextricably linked to one another, it being possible for the invention to relate to only one of these structural or functional features, or only a part of these structural or functional features, or only a part of one of these structural or functional features, or any grouping, combination or juxtaposition of all or part of these structural or functional features.

BRIEF DESCRIPTION OF THE FIGURES

Other aims, features and advantages of the invention will become apparent on reading the following nonlimiting detailed description of some possible embodiments, with reference to the appended figures, in which:

FIGS. 4a and 4b show schematic views of a receiving actuator of an orthopaedic device according to the invention;

FIGS. 5a and 5b show schematic views of a receiving actuator of an orthopaedic device according to the invention;

FIGS. 6a and 6b show schematic views of an emitting actuator of an orthopaedic device according to the invention;

FIGS. 7a and 7b show schematic views of an emitting actuator of an orthopaedic device according to the invention;

DESCRIPTION OF SOME EMBODIMENTS

In the figures illustrative of the invention, given solely non-limitingly, the proportions are not necessarily the actual proportions, this being solely for the sake of clarity of the disclosure.

Figure 1:
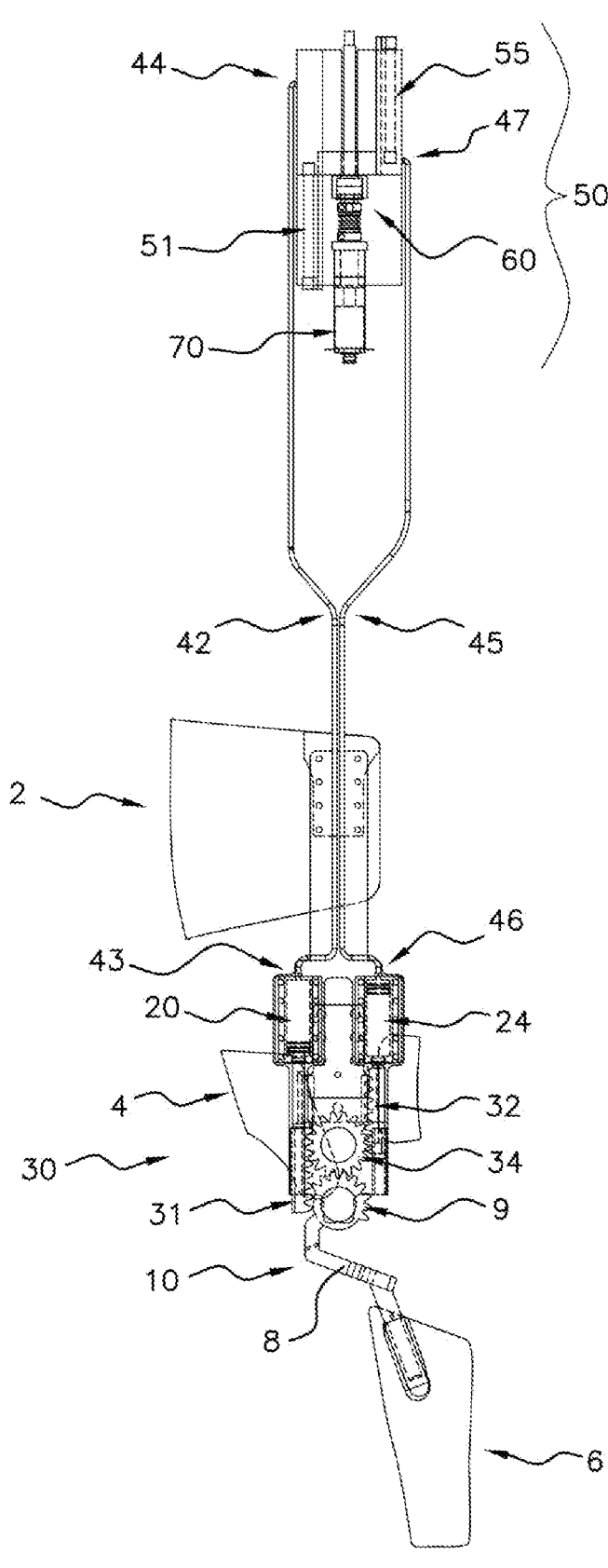
FIG. 1 shows a schematic view of an orthopaedic device according to the invention.
Figure 2:
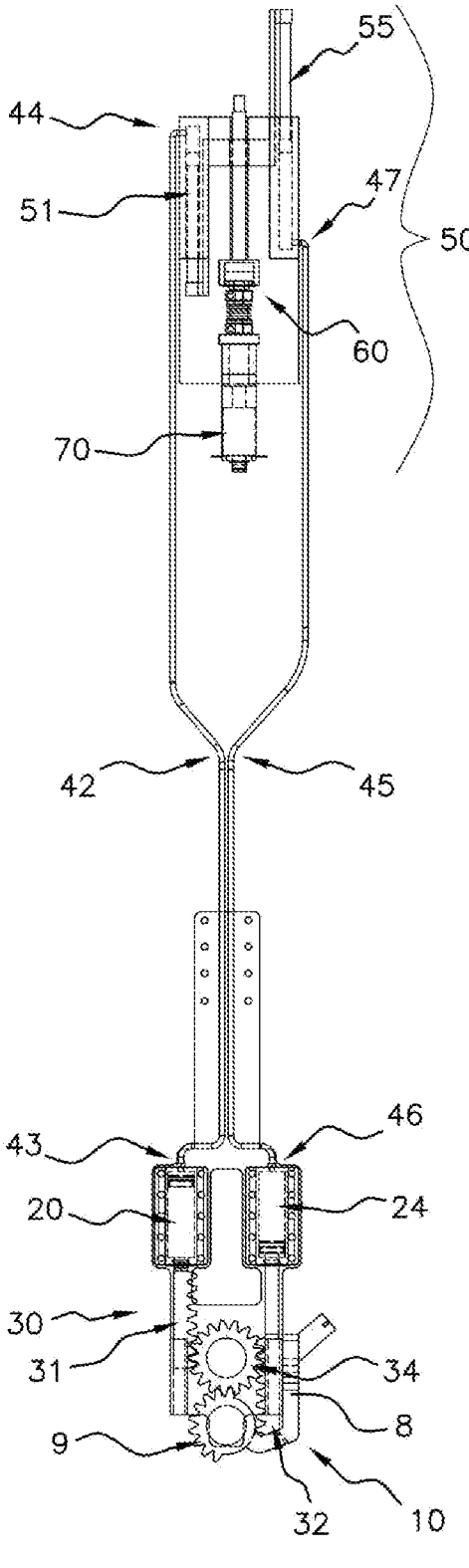
FIG. 2 shows a schematic view of an orthopaedic device according to the invention (without exoskeleton)
Figure 3:
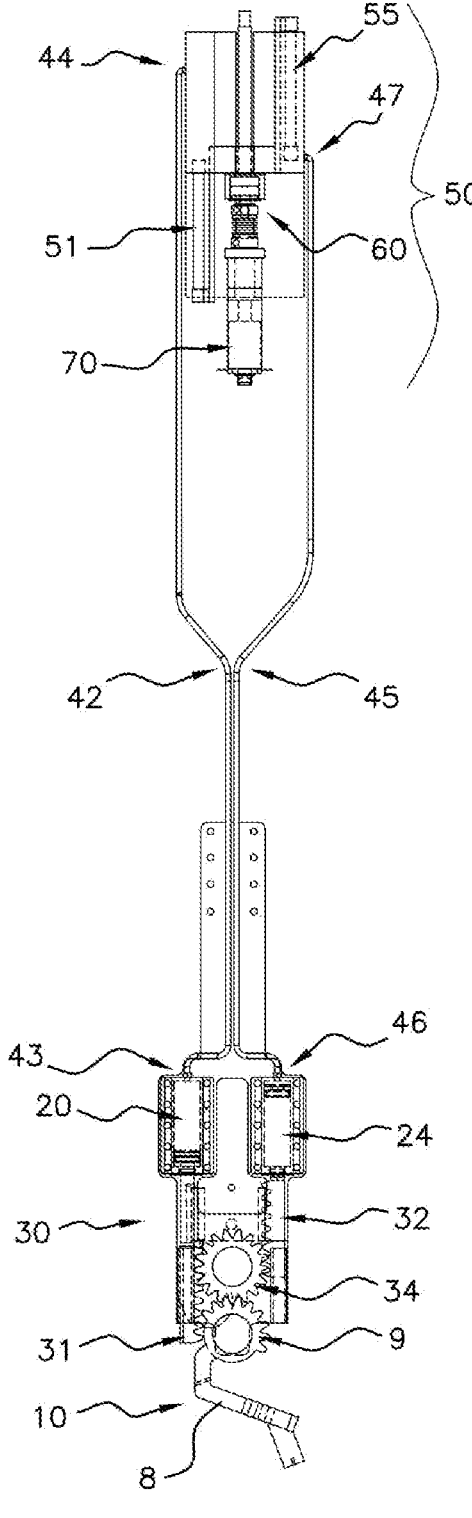
FIG. 3 shows a schematic view of an orthopaedic device according to the invention (without exoskeleton)

The orthopaedic device illustrated in FIGS. 1, 2 and 3 comprises an upper exoskeleton and a lower exoskeleton 6 hinged with respect to one another by a pivot-connection member 10. Here, as can be seen in FIG. 1, the upper exoskeleton comprises a portion 2 arranged on the top of the thigh and a portion 4 surrounding the bottom part of the thigh, above the knee. The lower exoskeleton 6 comprises a portion abutting the calf of the lower limb equipped with the orthopaedic device.

The pivot-connection member comprises a bottom toothed wheel 9 fixed to a lever connected to the lower exoskeleton 6. The lever 8 may be in the form of a bent metal rod or a bar having multiple curved and/or straight portions juxtaposed with one another.

The orthopaedic device comprises a receiving transmission device 30 designed to be able to transmit a movement and a force to the pivot-connection member 10. The receiving transmission device 30 as illustrated in FIG. 1 is of the rack-pinion type.

The orthopaedic device comprises a receiving actuator coupled to the receiving transmission device 30 so as to be able to rotate the pivot-connection member 10. The receiving actuator comprises a first hydraulic receiving cylinder 20 and a second hydraulic receiving cylinder 24.

The first hydraulic receiving cylinder 20 moves a first rack 31, which meshes with a top toothed wheel 34, in translation. The second hydraulic receiving cylinder 24 moves a second rack 32, which likewise meshes with the top toothed wheel 34, in translation. The bottom toothed wheel 9 of the pivot-connection member 10 likewise meshes with the top toothed wheel 34. The first rack 31 and the second rack 32 extend longitudinally and parallel to one another. In this case, the receiving transmission device 30 therefore has a double pinion and double rack configuration.

The first hydraulic receiving cylinder 20 and the second hydraulic receiving cylinder 24 are actuated via two pressurized-fluid-guiding lines 42 and 45, respectively. The two pressurized-fluid-guiding hydraulic lines 42 and 45 are powered by an emitting actuator 50, the latter being offset physically with respect to the receiving actuator, thus making it possible to offset it with respect to the leg and to the knee of the user. Each fluid-guiding hydraulic line 42, 45 is connected respectively to the first hydraulic receiving cylinder 20 and the second hydraulic receiving cylinder 24 via a fluidic communication orifice 43 and 46 in each hydraulic receiving cylinder 20, 24, as can be seen in FIGS. 1 to 3.

The emitting actuator 50 comprises a first hydraulic emitting cylinder 51 and a second hydraulic emitting cylinder 55, which are connected to an emitting transmission device 60 designed to be able to transmit a movement and a force to the emitting cylinders 51, 55. The emitting transmission device 60 shown in FIGS. 1, 2 and 3 is of the screw-nut type.

The emitting actuator 50 comprises a motor device 70 coupled to the emitting transmission device 60 in order to be able to drive the hydraulic emitting cylinders 51, 55. The emitting transmission device 60 shown in FIGS. 1, 2 and 3 is of the screw-nut type. A rotor of the motor device 70 is coupled to the screw of the emitting transmission device 60, this screw interacting with the thread of a nut connected mechanically to the respective pistons of the first hydraulic emitting cylinder 51 and of the second hydraulic emitting cylinder 55. The first hydraulic emitting cylinder 51 and the second hydraulic emitting cylinder 55 are installed in opposition such that when the nut of the emitting transmission device 60 is moved in translation by the rotational action of the screw of the emitting transmission device 60, the piston of the first hydraulic emitting cylinder 51 enters its cylinder and the piston of the second hydraulic emitting cylinder 55 leaves its cylinder, and vice versa. Thus, depending on the direction of translational movement of the nut of the emitting transmission device 60, a pressure difference is brought about in the first hydraulic emitting cylinder 51 or the second hydraulic emitting cylinder 55. The first hydraulic emitting cylinder 51 and the second hydraulic emitting cylinder 55 in turn supply pressurized fluid to the fluid-guiding hydraulic lines 42 and 45. Each fluid-guiding line 42, 45 is connected respectively to the first hydraulic emitting cylinder 51 and to the second hydraulic emitting cylinder 55 via a fluidic communication orifice 44, 47 in each emitting cylinder 51, 55, as can be seen in FIGS. 1 to 3. FIGS. 2 and 3 illustrate the bending and extension, respectively, of the leg to which the orthopaedic device would be fixed.

In another embodiment of an orthopaedic device according to the invention, the receiving actuator as illustrated in FIGS. 4a and 4b may comprise a first hydraulic receiving cylinder 22 and a spring 23. In this case, the orthopaedic device comprises only a single fluid guiding line 48. The transmission device of such a receiving actuator illustrated in FIGS. 4a and 4b is of the pinion-rack type. The first hydraulic receiving cylinder 22 moves a rack 35 and the spring 23 moves a rack 36. FIGS. 4a and 4b illustrate the bending and extension, respectively, of the leg to which the orthopaedic device would be fixed. The bar in bold in the form of an inverted T in FIGS. 4a, 4b connecting the hydraulic receiving cylinder 22, the spring 23 and the connection member 10 schematically depicts a fixed part of the stator type connecting these elements of the orthopaedic device (in practice, this is a plate to which is likewise fixed the upper exoskeleton, for example).

In another embodiment of an orthopaedic device according to the invention, the receiving actuator as illustrated in FIGS. 5a and 5b may comprise a first double-acting hydraulic receiving cylinder 26 and a second double-acting hydraulic receiving cylinder 27. The first hydraulic receiving cylinder 26 and the second hydraulic receiving cylinder 27 are connected to one another by a fluidic communication tube 28. The transmission device of such a receiving actuator illustrated in FIGS. 5a and 5b is of the type comprising a cable 80 connected by one end to the piston of the first hydraulic receiving cylinder 26 and by another end to the second hydraulic receiving cylinder 27. FIGS. 5a and 5b illustrate the bending and extension, respectively, of the leg to which the orthopaedic device would be fixed.

In another embodiment of an orthopaedic device according to the invention, the emitting actuator as illustrated in FIGS. 6a and 6b (configurations corresponding to bending and extension) comprises a first hydraulic emitting cylinder 85, a second hydraulic emitting cylinder 86 and a mechanical transmission device 84 of the pinion-rack type comprising two racks 81, 82 actuated by a pinion 83 comprising a motor device which rotates it. Each hydraulic cylinder 85, 86 is connected to a fluid-guiding hydraulic line 87, 88, respectively.

In another embodiment of an orthopaedic device according to the invention, the emitting actuator as illustrated in FIGS. 7a and 7b (configurations corresponding to bending and extension) comprises a double-acting cylinder 90 connected to fluid-guiding hydraulic lines 97, 98, and an emitting transmission device 92 of the screw-nut type coupled to a motor device 95.

The orthopaedic device may comprise sensors 106, such as accelerometers, position sensors, pressure sensors, twisting-torque sensors, force sensors or deformation sensors.

The orthopaedic device comprises an electronic unit 100 and a man/machine interface 105. The man/machine interface 105 may comprise any type of display screen (computer, mobile telephone, tablet, etc.) and allows a user to define the operating parameters of the orthopaedic device. Such sensors and the data communicated to the electronic unit 100 make it possible to detect an intention of movement on the part of the user equipped with the orthopaedic device.

Figure 8:
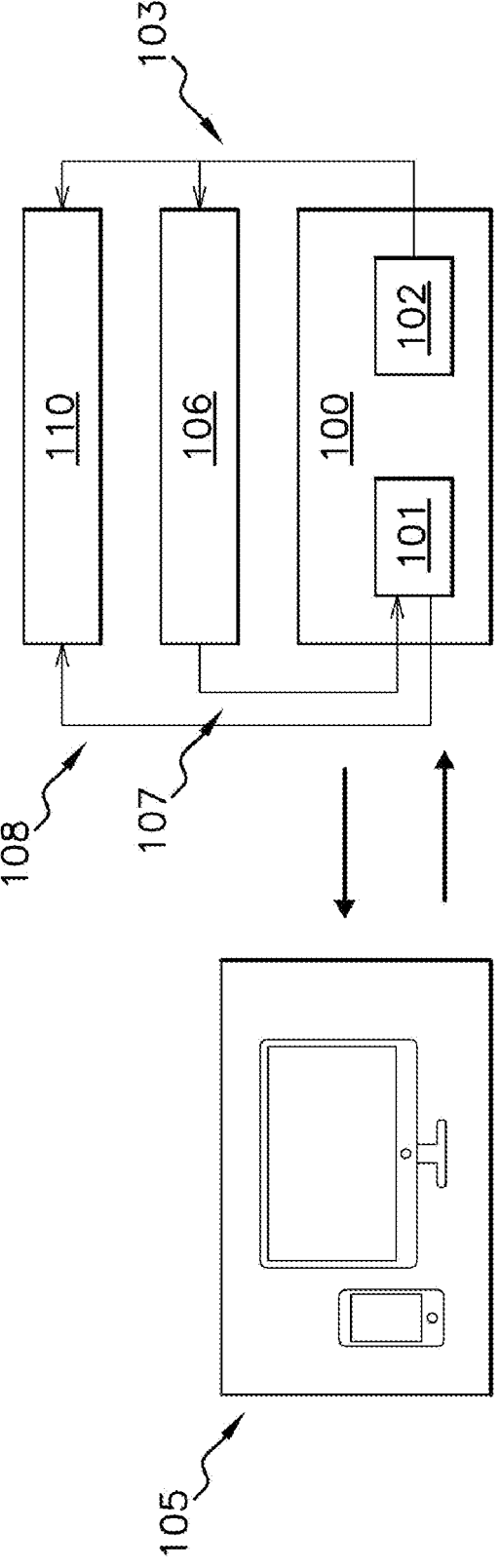
FIG. 8 shows a schematic view of the control architecture of an orthopaedic device according to the invention.

FIG. 8 illustrates the control architecture of an orthopaedic device according to the invention. The electronic unit 100 comprises a control unit 101 for controlling the exoskeleton (that is to say the upper exoskeleton and the lower exoskeleton) and an electrical power supply unit 102. The power supply unit 102 supplies the necessary electrical power to the sensors 106 and to the emitting actuator schematically depicted by the box 110 in FIG. 8, as illustrated by the arrow 103. As illustrated by the double arrow in FIG. 8 between the man/machine interface 105 and the electronic unit 100, the selection of an operating mode for example is communicated to the exoskeleton control unit 101 via the man/machine interface 105 and data representative of the operation of the orthopaedic device (in particular the measurements carried out by the sensors) are transmitted to the man/machine interface 105. The arrow 108 symbolizes the controls given by the exoskeleton control unit 101 to the emitting actuator schematically depicted by the box 110. And the arrow 107 symbolizes the data sent in return by the sensors 106 (or other instruments) to the exoskeleton control unit 101.

The orthopaedic device is controlled using a feedback loop between the motor device of the emitting actuator and the signals transmitted by said sensors. When the orthopaedic device detects a user's intention to move the leg, a high-level control law of the electronic unit defines a command (a torque or a predetermined rotation) to be applied to the pivot-connection member. A low-level control law of the electronic unit then slaves the electrohydraulic mechanism so as to apply the predefined command to the pivot-connection member of the orthopaedic device.

In the embodiment of an orthopaedic device shown in FIGS. 1 to 3, for an extension movement of the leg (FIG. 3), the motor device 70 rotates in the anticlockwise direction, thereby moving the nut of the emitting transmission device 60 of the emitting actuator towards the motor device 70. This leads to a double action on the emitting cylinders 51 and 55 of the emitting actuator: a negative relative pressure difference is brought about in one of them, whereas a positive relative pressure difference is brought about in the other. The fluid-guiding hydraulic lines 42 and 45 transmit the pressure variation to the receiving cylinders 20, 24, thereby allowing a force to be transmitted to the racks 31, 32 and therefore a torque to be transmitted to the bottom toothed wheel 9 and the top toothed wheel 34. The lower exoskeleton 6 is rotated about the pivot axis of the pivot-connection member in the clockwise direction and thus helps to extend the leg of the user.

In the embodiment of an orthopaedic device shown in FIGS. 1 to 3, for a bending movement of the leg (FIG. 2), the motor device 70 rotates in the clockwise direction, thereby moving the nut of the emitting transmission device 60 of the emitting actuator with respect to the motor device 70. This leads to a double action on the emitting cylinders 51 and 55 of the emitting actuator: a positive relative pressure difference is brought about in one of them, whereas a negative relative pressure difference is brought about in the other. The fluid-guiding hydraulic lines 42 and 45 transmit the pressure variation to the receiving cylinders 20, 24, thereby allowing a force to be transmitted to the racks 31, 32 and therefore a torque to be transmitted to the bottom toothed wheel 9 and the top toothed wheel 34. The lower exoskeleton 6 is rotated about the pivot axis of the pivot-connection member 10 in the anticlockwise direction and thus helps to bend the leg of the user.

Figure 9:
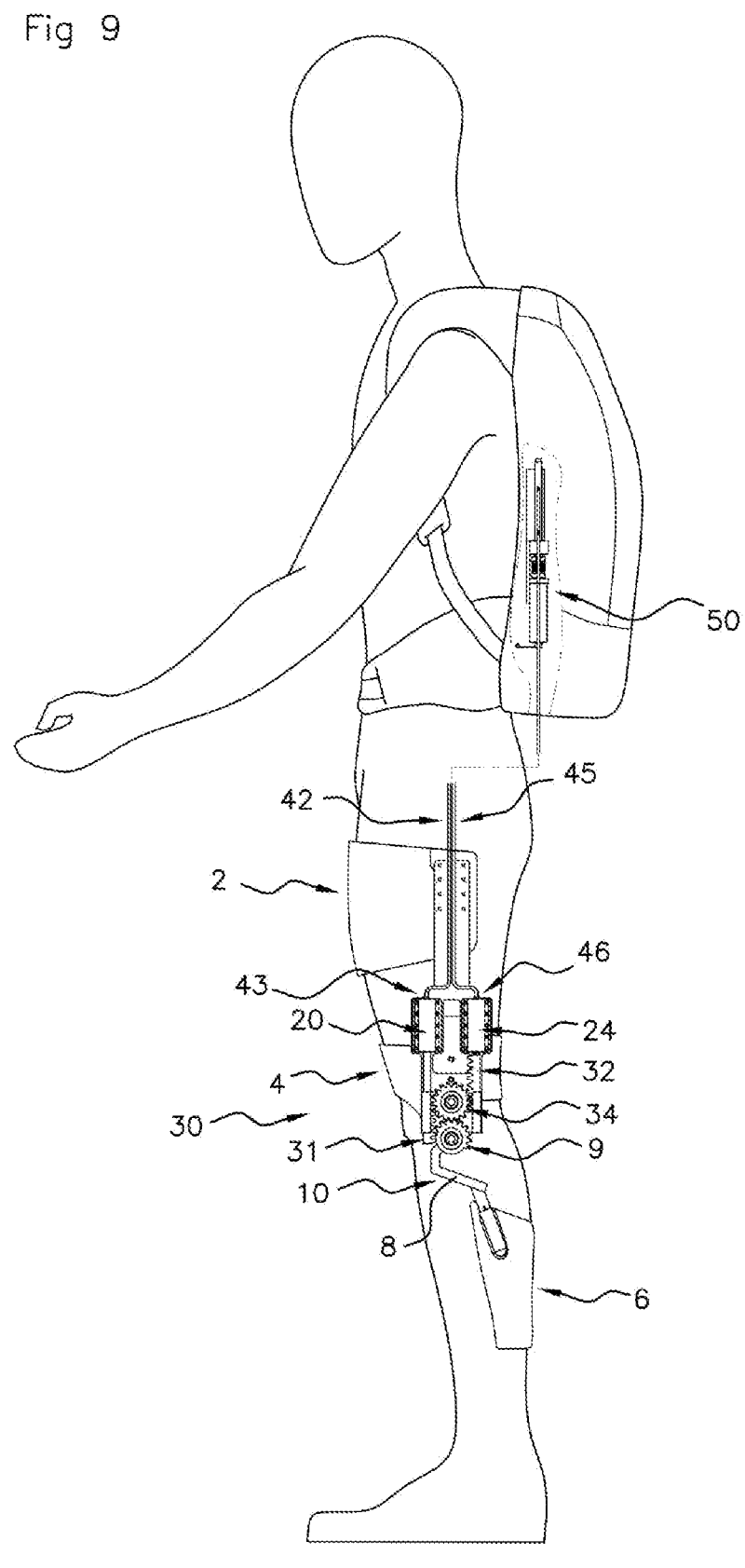
FIG. 9 shows a schematic profile view of a user equipped with an orthopaedic device according to the invention.

FIG. 9 illustrates an orthopaedic device according to the invention with which a user is equipped. In the embodiment illustrated, the orthopaedic device corresponding to the embodiment illustrated in FIGS. 1 to 3 equips a user wearing a backpack in which the emitting actuator is disposed. It should be noted that provision may be made for each actuator to be disposed in a casing (not shown) in order to facilitate their handling and to protect them.

The portions of the upper exoskeleton 2, 4 and of the lower exoskeleton 6 as shown in FIG. 1 may have numerous other shapes or be disposed in abutment against other parts (as an alternative to or in combination with) the lower limb. They may comprise adjusting straps or any other adjusting and/or fixing device so as to be able to adapt to any type of body shape. It is likewise possible to make each portion of the upper exoskeleton 2, 4 and of the lower exoskeleton 6 bespoke for each user depending on the pathologies or the body shape of each user.

The invention can be varied and applied in numerous ways other than those described above. In particular, it goes without saying that, unless indicated otherwise, the various structural and operational features of each of the embodiments described above should not be considered to be combined with and/or intrinsically and/or inextricably linked to one another, but by contrast to be simple juxtapositions. Moreover, the structural and/or operational features of the various embodiments described above may be juxtaposed differently or combined differently as a whole or in part.

In particular, this description is given solely by way of illustrative example. A person skilled in the art will be able to envision numerous modifications, other than the variants mentioned in the course of the description above, without departing from the scope of the invention. An orthopaedic device according to the invention may likewise be in the form of a hip orthosis or a whole-leg orthosis, for example.

The invention claimed is:

1. An orthopaedic device, comprising:
   at least one portion, referred to as an upper exoskeleton, suitable for forming an abutment in contact with a first part of the human body,
   at least one portion, referred to as a lower exoskeleton, suitable for forming an abutment in contact with a second part of the human body,
   an actuator, referred to as a receiving actuator, comprising:
      a pivot-connection member having at least one pivot axis, said upper exoskeleton and said lower exoskeleton being hinged with respect to one another via said pivot-connection member, a receiving transmission device designed to be able to transmit a movement to the pivot-connection member, and
      at least a first hydraulic cylinder, referred to as a first receiving cylinder, coupled to the receiving transmission device so as to be able to rotate the pivot-connection member,
   an actuator, referred to as an emitting actuator, comprising:
      a motor device, and
      two hydraulic cylinders, referred to respectively as a first emitting cylinder and a second emitting cylinder, each comprising a piston and an associated cylinder, and
   two pressurized-fluid-guiding hydraulic lines connected to the first emitting cylinder and to the second emitting cylinder, respectively, and designed to allow a hydraulic transmission of movement from the emitting actuator to the receiving actuator,
   wherein the emitting actuator further comprises an emitting transmission device of a screw-nut type coupled to the motor device;
   a rotor of the motor device is coupled to a screw of the emitting transmission device, this screw interacting with the thread of a nut connected mechanically to the respective pistons of the first emitting cylinder and of the second emitting cylinder; and
   the first emitting cylinder and the second emitting cylinder are installed in opposition and mechanically connected to the nut of the emitting transmission device such that when said nut is moved in translation by a rotational action of the screw of the emitting transmission device, the piston of the first emitting cylinder enters the associated cylinder and the piston of the second hydraulic emitting cylinder leaves the associated cylinder, and vice versa.

2. The device according to claim 1, wherein the first and second emitting cylinders of the emitting actuator are selected from among single-acting cylinders and double-acting cylinders.

3. The device according to claim 1, wherein the motor device of the emitting actuator is an electric motor, a hydraulic motor or a pneumatic motor.

4. The device according to claim 1, wherein the receiving actuator comprises a second cylinder, referred to as a second receiving cylinder, the first receiving cylinder and said second receiving cylinder being connected to one of the two pressurized-fluid-guiding hydraulic lines, respectively.

5. The device according to claim 4, wherein the first and second receiving cylinders of the receiving actuator are single-acting cylinders or double-acting cylinders.

6. The device according to claim 1, wherein the receiving transmission device is selected from the group formed by mechanical transmissions designed to be able to transform a translational movement transmitted by the receiving actuator into a rotational movement of the pivot-connection member.

7. The device according to claim 1, wherein the receiving transmission device is selected from the group formed by mechanical cable and/or belt transmissions, transmissions of a rod-crank type, and mechanical transmissions of a pinion-rack type.

8. The device according to claim 1, further comprising an electronic unit for defining a command to be applied to the pivot-connection member and a man/machine interface for allowing a user to define operating parameters of the orthopaedic device.

9. The device according to claim 1, further comprising at least one sensor selected from the group formed by accelerometers, position sensors, pressure sensors, twisting-torque sensors, force sensors and deformation sensors.

10. The device according to claim 1, wherein the pivot-connection member comprises a bottom toothed wheel and a lever which is connected to the lower exoskeleton and is in a form of a bar having multiple curved and/or straight portions juxtaposed with one another, said pivot-connection member being designed to permit at least two portions of said metal bar to rotate with respect to one another about an axis orthogonal to the pivot axis of the pivot-connection member such that said pivot-connection member may exhibit one or more degrees of adjustment out-of-plane, in order to be able to better adapt to a user's gait.

11. The device according to claim 1, wherein the pivot-connection member is a polycentric pivot-connection member.

12. The device according to claim 11, wherein the polycentric pivot-connection member is adapted to a kinematics of a joint between the first part and the second part of the human body in contact with which the upper exoskeleton and the lower exoskeleton can be rested.

13. The device according to claim 1, further comprising a backpack in which the emitting actuator is installed.

* * * * *